(12) United States Patent
Padmanabhan et al.

(10) Patent No.: US 8,287,700 B2
(45) Date of Patent: Oct. 16, 2012

(54) METHODS AND PROCESSES FOR ATTACHING COMPOUNDS TO MATRICES

(75) Inventors: Seetharamaiyer Padmanabhan, Lexington, MA (US); Radhakrishnan P. Iyer, Shrewsbury, MA (US)

(73) Assignee: Spring Bank, Milford, MA (US)

( * ) Notice: Subject to any disclaimer, the term of this patent is extended or adjusted under 35 U.S.C. 154(b) by 146 days.

(21) Appl. No.: 12/641,002

(22) Filed: Dec. 17, 2009

(65) Prior Publication Data
US 2010/0096251 A1    Apr. 22, 2010

Related U.S. Application Data

(62) Division of application No. 11/095,077, filed on Mar. 31, 2005, now abandoned.

(60) Provisional application No. 60/558,778, filed on Apr. 1, 2004, provisional application No. 60/583,413, filed on Jun. 28, 2004, provisional application No. 60/616,388, filed on Oct. 6, 2004.

(51) Int. Cl.
*C07D 213/61* (2006.01)
*C07H 21/04* (2006.01)

(52) U.S. Cl. ......... 204/157.71; 204/157.64; 204/157.63; 204/157.6; 204/157.87

(58) Field of Classification Search ............ 204/157.71, 204/157.87, 157.64, 157.63, 157.6
See application file for complete search history.

(56) References Cited

U.S. PATENT DOCUMENTS

| | | | |
|---|---|---|---|
| 6,444,111 B1 | 9/2002 | Montgomery | |
| 6,617,162 B2 | 9/2003 | Dobie et al. | |
| 6,825,032 B2 | 11/2004 | Dapron et al. | |
| 6,984,485 B2 | 1/2006 | Matson | |
| 7,195,874 B2 | 3/2007 | Rothschild et al. | |
| 7,195,913 B2 | 3/2007 | Guire et al. | |
| 2003/0027982 A1 | 2/2003 | Gutheil et al. | |
| 2003/0082633 A1 | 5/2003 | Martin et al. | |
| 2009/0012264 A1 | 1/2009 | Collins et al. | |

FOREIGN PATENT DOCUMENTS

DE    100 06 138.9    8/2000

OTHER PUBLICATIONS

Beier et al , Nucleic acids Research, 199, 27(9), pp. 1970-1977.*
Lidstrom et al., "Microwave assisted organic synthesis—a review," Tetrahedron, 57: 9225-9283 (2001).
Caruthers et al., "Chemical Synthesis of Deoxyoligonucleotides by the Phosphoramidite Method", Methods in Enzymology, 154: 287-313 (1987).
Pon et al., "Rapid Esterification of Nucleosides to Solid-Phase Supports for Oligonucleotide Synthesis Using Uronium and Phosphonium Coupling Reagents", Bioconjugate Chem., 10: 1051-1057 (1999).
Olsson et al., "Microwave-assisted Solvent-free Parallel Synthesis of Thioamides", Tetrahedron Letters, 41: 7947-7950 (2000).
Dallinger et al., "Microwave-assisted Scavenging of Electrophiles Utilizing Polymer-Supported Sequestration Reagents. Application to the Synthesis of N3-acylated Dihydropyrimidine Libraries", Molecular Diversity, 7: 229-245 (2003).
Stadler et al., "The Effect of Microwave Irradiation on Carbodiimide-Mediated Esterifications on Solid Support", Tetrahedron, 57: 3915-3920 (2001).
Larhed et al., "Microwave-Promoted Palladium-Catalyzed Coupling Reactions", J. Org. Chem., 61: 9582-9584 (1996).
Eynde et al., "Microwave-mediated Derivatization of Poly(stryene-co-allyl alcohol), a Key Step for the Soluble Polymer-assisted Synthesis of Heterocyles", Tetrahedron, 55: 2687-2694 (1999).
Ganschow et al., "Anchoring of Functional Dye Molecules in MCM-41 by Microwave-Assisted Hydrothermal Cocondensation", Angew. Chem. Int.Ed. 39(1): 161-163 (2000).
Hoel et al. "Microwave-Assited Solid-Phase Ugi Four-Component Condensations", Tetrahedron Letters, 40: 3941-3944 (1999).

* cited by examiner

*Primary Examiner* — T. D. Wessendorf
(74) *Attorney, Agent, or Firm* — Edwards Wildman Palmer LLP; Peter F. Corless; Weiying Yang

(57) ABSTRACT

The present invention describes extremely rapid and efficient methods for the attachment of chemical moieties to matrices by the use of microwave technology. The methods of the invention can be applied in a variety of ways for the preparation of different types of matrices for a variety of applications including but not limited to the functionalization of various solid supports, and matrices in the form of powder, beads, sheets, and other suitable surfaces for use in applications including but not limited to oligonucleotide synthesis, peptide synthesis, environmental clean up (removal of toxic materials), immunoassays, affinity chromatography, combinatorial chemistry, microarrays, proteomics and medical diagnostics.

13 Claims, No Drawings ly. Consequently, the initial attachment of the chemical moiety to the matrix is the rate-limiting step. Furthermore, an important parameter for the use of any matrix is the "loading of the support" (expressed as micromol/g) with the chemical moiety. A low loading would necessitate the use of larger amounts of the matrix to accomplish a desired application objective. This results in substantial increase in cost. The loading protocols employ hazardous solvents and reagents and takes long reaction times. The commonly employed loading processes are also inefficient since, often incomplete reaction results in "uncapped" functionalities on the solid matrix. Thus e.g., when a loaded matrix is employed in solid-phase synthesis, uncapped functionalities on the solid matrix would interfere with the subsequent synthetic steps thereby decreasing the overall yield of the desired product. Thus an additional "capping step" needs to be employed before the matrix can be used in synthesis.

METHODS AND PROCESSES FOR ATTACHING COMPOUNDS TO MATRICES

RELATED APPLICATIONS

This application is a divisional of U.S. application Ser. No. 11/095,077, filed Mar. 31, 2005, which claims the benefit of U.S. Provisional Application No. 60/558,778, filed on Apr. 1, 2004, U.S. Provisional Application No. 60/583,413, filed on Jun. 28, 2004 and U.S. Provisional Application No. 60/616,388, filed on Oct. 6, 2004. The entire teachings of the above applications are incorporated herein by reference.

GOVERNMENT SUPPORT

The invention was supported, in whole, or in part, by NIH grant number 5 UO1 AI058270-02. The Government has certain rights in the invention.

FIELD OF THE INVENTION

This invention relates to novel methods of attaching chemical moieties to inorganic and organic matrices. The matrices carrying such chemical moieties can be used in a number of applications such as in solid-phase synthesis, diagnostic devices, biosensors, catalysts, scavengers, and in drug delivery systems.

BACKGROUND OF INVENTION

Since the first report of solid-phase synthesis of peptides by Merrifield in 1962, several applications of using solid matrices have evolved over the past 50 years. For example, solid-phase synthesis is now routinely employed for the synthesis and manufacture of macromolecules such as peptides, carbohydrates, and oligonucleotides. Also, several organic reactions are routinely performed in solution phase employing reagents that are covalently bound to solid matrix. Following the reaction, the matrix containing the reagent is simply filtered off from the reaction medium enabling partial purification of the desired product from the solution. In another application, compounds attached to solid matrices that carry acidic and basic moieties are employed as "scavengers" of basic and acidic reagents respectively from reaction media.

Several catalysts employed in organic synthesis are often employed as solid matrix. Compounds attached to solid matrices are also employed as sensors in detection devices. In yet another application, drug molecules attached to solid matrices are used as delivery systems for topical and systemic administration of drugs.

Macromolecules such as oligonucleotides as antisense compounds and as agents of RNA interference are synthesized and manufactured routinely using solid-phase synthesis. In this case, the first nucleotidic or amino acid residue (also referred to as the leader building block) is covalently attached to the solid matrix via a linker arm. The subsequent addition of monomeric units to the leader block is carried out on the solid matrix. Upon completion of the assembly of the macromolecule, the matrix is treated with a chemical reagent that cleaves the linker arm of the leader block thereby releasing the macromolecule into solution.

The attachment of chemical moiety to the matrix is a very important step for various applications of the matrices. Usually the chemical moiety is employed as a solution, which is then contacted with the matrix with and without the aid of a catalyst or other reagent. Since this is a biphasic reaction involving solid and liquid matrix, reaction times can often vary from several hours even into days before complete reaction occurs. Consequently, the initial attachment of the chemical moiety to the matrix is the rate-limiting step. Furthermore, an important parameter for the use of any matrix is the "loading of the support" (expressed as micromol/g) with the chemical moiety. A low loading would necessitate the use of larger amounts of the matrix to accomplish a desired application objective. This results in substantial increase in cost. The loading protocols employ hazardous solvents and reagents and takes long reaction times. The commonly employed loading processes are also inefficient since, often incomplete reaction results in "uncapped" functionalities on the solid matrix. Thus e.g., when a loaded matrix is employed in solid-phase synthesis, uncapped functionalities on the solid matrix would interfere with the subsequent synthetic steps thereby decreasing the overall yield of the desired product. Thus an additional "capping step" needs to be employed before the matrix can be used in synthesis.

Clearly, efficient processes for attaching chemical moieties to different types of matrices will be of great value in the use of the matrices for different applications.

SUMMARY OF INVENTION

The present invention describes extremely rapid and efficient methods for the attachment of chemical moieties to matrices by the use of microwave technology. The methods of the invention can be applied in a variety of ways for the preparation of different types of matrices for a variety of applications including but not limited to the functionalization of various solid supports, and matrices in the form of powder, beads, sheets, and other suitable surfaces for use in applications including but not limited to oligonucleotide synthesis, peptide synthesis, environmental clean up (removal of toxic materials), immunoassays, affinity chromatography, combinatorial chemistry, microarrays, proteomics and medical diagnostics.

DETAILED DESCRIPTION OF THE INVENTION

With the recent advances in genomics and proteomics, small molecules and macromolecules have been discovered against disease targets and have shown promise as potential drug candidates. However several analogs of these early stage compounds need to be synthesized and tested for lead optimization. Most synthetic processes are slow and time consuming. Consequently, the advancement of early lead compounds by way of synthesis and testing is a slow process. The rapid synthesis and testing of many compounds will help accelerate lead optimization and drug development.

Most developments in chemistry have been concerned with highly reactive reagents in solution or solid phase. The energy for most chemical reactions is provided by heat transfer equipment such as oil baths, sand baths and heating jackets in contact with the reaction vessel. These methods of heat transfer are inefficient resulting in slow and non-uniform heating of reactants. In contrast, Microwave energy has been found to induce dramatic rate accelerations of chemical reactions. During the past 20 years, it has been found that a large number of chemical reactions that took several hours and days to complete can be done in less than five minutes through the intervention of microwave energy. This is because microwave radiation induces dielectric heating and almost all the energy associated with it is used to directly heat the reactants and solvents and not the reaction vessel. Microwave radiation passes through the walls of the vessel and heats only the reactants and the solvent and not the reaction vessel itself. In a properly designed apparatus, the temperature will be uniform throughout the reaction media and therefore there is less likelihood of byproducts and decomposition products.

If the reaction vessel is kept under pressure, rapid increases in temperature can result that are much higher than the boiling point of the solvent. The reason for this is two fold: microwave radiation has both an electric field and magnetic field component. The former is responsible for heating. The heat is generated by rapid kinetic energy (rotational and vibrational energy) released by alignment of the dipoles of the dilelectic solvent with the applied electric field. Another factor which results in heating is the conductance process due to presence of ions in the medium that increases the collision rate converting the kinetic energy into heat. Consequently, to be effective in the microwave process, the solvents that are employed should have a high dilectric constant. These solvents include, water, (dimethyl sulfoxide (DMSO), DMF (Dimethyl formamide), dimethyl acetamide, N-methyl pyrrolidone, acetonitrile ($CH_3CN$), Methanol, ethanol, acetone etc. However, the inherent hazard of violent explosions due to higher pressures and temperature developed in close vessel under microwave radiation has led to modified protocols in some cases. Heavy-walled reaction chambers with pressure release systems and solvent-less reactions have led to more and safer operations.

A number of reactions have been described in the literature that have successfully utilized microwave processes. These include N-acylation, alkylation, nucleophilic substitutuion, aromatic substitution, cycloaddition, deprotection and protection of functional groups, esterification and transesterification, heterocycle synthesis, organometallic reactions, oxidations, rearrangements, and reductions. Several "name reactions" such as Diels-Alder, Knoevenagel condensations, Hech and Suzuki couplings etc. are included in the above list. (Lidstrom, P., Terry, J., Wathey, B., Westman, J. Tetrahedron, 2001, 57, 9225).

It is pertinent to mention that microwave reactions have also been employed both in solution-phase and solid-phase reactions. For example, Larhed et al., (Larhed, M., Hallberg, A. J. Org. Chem. 1996, 61, 9582) used microwave to enable solid-phase Suzuki coupling reactions. Ugi "four-component" reactions have been done in solid-phase using microwave (Hoel, A. M. L., Nielsen, J. Tetrahedron Lett., 1999, 40, 3941-44). Heterocycles such as succinimide have been synthesized on an amine-terminated polystyrene resin upon reaction with substituted succinic anhydrides in the presence of $TaCl_3$-$SiO_2$ catalysis (Chandrasekhar, S., Padmaja, M. B., Raza, A. Synlett. 1999, 10, 1597). Other examples include transesterifications of allyl alcohol teriminated polystyrene soluble polymer with acetoacetic ester (Vanden Eynde, J. J., Rutot, D. Tetrahedron, 1999, 55, 2687), hydrothermal co-condensation on solid support (Ganschow, M., Wark, M., Wohrle, D., Schulz-Ekloff, G. Angew Chem Intl. Ed. Engl. 2000, 1, 161. However, most reactions have been reported in solution-phase.

Although as stated above, microwave-assisted processes have been employed in solid-phase synthesis, there is no report of microwave-assisted loading of building blocks on to solid supports. Several applications of the novel, microwave-assisted processes of the invention are anticipated. For example, the functionalized solid-support can be readily loaded with nucleosides for use in oligonucleotide synthesis in accordance with the invention. Starting from (un-derivatized), native controlled-pore-glass (CPG), complete functionalization and loading of nucleosides can be done within 24 to 48 hours ready for DNA synthesis using the methods of the invention. The conventional procedures require between 7 to 10 days to obtain fully loaded supports. Using the present invention, nucleoside-loaded supports can be made cheaper, faster and more eco-friendly. Several 100 g batches of the supports with consistent high loadings of 70 to 80 micromol/g have been obtained as discussed in the Examples. Consequently, this process will be very useful both for smaller scale, and larger-scale operations.

Another application of the invention relates to the rapid preparation of functionalized matrices for applications in microarrays, proteomics, medical diagnostics, and the like. In yet another application of the invention, rapid preparation of functionalized supports for loading with amino acids, nucleoside derivatives, sugars and other carbohydrates, small molecules, antibodies, proteins, amino acids, peptides, and other ligands and macromolecules, for a variety of applications including peptide and carbohydrate synthesis and environmental clean up (removal of toxic materials), radioimmunassays (RIAs), fluorescence immunoassays (FIAs), ELISA, and Affinity Chromatography is made possible.

In one embodiment, the invention provides a method for attaching a chemical moiety to a matrix comprising the steps of: (a) contacting the matrix with a reagent capable of a nucleophilic group such as an amino, hydroxyl, or carboxylic group to the matrix; (b) exposing the reaction mixture of step (a) to microwave radiation thereby resulting in a functionalized matrix; (c) contacting the functionalized matrix of step (b) with a reagent capable of forming an ester or amide bond with the matrix and further comprising free carboxyl termini on the matrix; (d) exposing the reaction mixture of step (c) to microwave radiation thereby forming a mono-ester or mono-amide linkage with the matrix comprising free carboxyl termini on the matrix; and (e) contacting the carboxylated matrix of step (d) with the chemical moiety via a functionalized region of the chemical moiety capable of reacting with the carboxylated matrix thereby resulting in a matrix functionalized with the chemical moiety such as amino, hydroxyl, or thiol groups.

Suitable matrices include but are not limited to, controlled pore glass (CPG), glass in the form of any glass surface natural or modified including beads or powders, silica gel, alumina, polystyrene, tentagel, polyethylene glycol, cellulose, Teflon, and their derivatives, ceramic, zeolite, clay, as well as, matrices such as, Ti, Carbon, Si, gold, or other metal surfaces. In a preferred embodiment, steps (a) and steps (c) of the above method are carried out in the presence of a solvent having a dielectric constant. Suitable solvents having dielectric constants include but are not limited to, dimethyl formamide, dimethyl acetamiide, N,N-dialkyl formamides and acetamides, N-methyl pyrrolidone, DMSO, and alcohols including polyols.

In a preferred embodiment, the exposing to microwave radiation steps of (b) and (d) comprises exposing the reaction mixtures to microwave radiation for a total time of at least about 4 minutes. The exposing steps may comprise pulsed radiation or constant microwave radiation.

For all embodiments described herein, suitable reagents capable of adding a nucleophilic group include but are not limited to, substituted and unsubstituted amines, alcohols and thiols.

For all embodiments described herein, suitable reagents capable of forming an ester or amide bond with the matrix and further comprising free carboxyl termini on the matrix such as substituted and unsubstituted amino acids, hydroxyl acids, thiol acids and halo acids.

For all relevant embodiments described herein, examples of functionalized regions of the chemical moieties that are capable of reacting with the carboxylated matrix include but are not limited to regions comprising,amino, hydroxyl, thiol, X—R reagents (where X is halogen, R is alkyl, aryl, aralkyl, cycloaclkyl, heterocyclics.

For all relevant embodiments described herein, examples of chemical moieties suitable for attachment to the functionalized matrices prepared in accordance with the invention include but are not limited to, modified and unmodified nucleosides and nucleotides, DNA, RNA, modified and unmodified amino acids, peptides, proteins, synthetic block polymers, heterocycles, organometallic synthesis reagents, lipids steroids and carbohydrates.

The term "nucleoside" as used herein refers to a heterocyclic nitrogenous base in N-glycosidic linkage with a sugar. Nucleosides are recognized in the art to include natural bases (standard), and modified bases well known in the art. Such bases are generally located at the 1' position of a nucleoside sugar moiety. Nucleosides generally comprise a base and sugar group. The nucleosides can be unmodified or modified at the sugar, and/or base moiety (also referred to interchangeably as nucleoside analogs, modified nucleosides, non-natural nucleosides, non-standard nucleosides and other; see for example, Usman and McSwiggen, supra; Eckstein et al., International PCT Publication No. WO 92/07065; Usman et al., International PCT Publication No. WO 93/15187; Uhlman & Peyman, supra, all are hereby incorporated by reference herein). There are several examples of modified nucleic acid bases known in the art as summarized by Limbach et al., 1994, Nucleic Acids Res. 22, 2183. Some of the non-limiting examples of chemically modified and other natural nucleic acid bases that can be introduced into nucleic acids include, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, quesosine, 2-thiouridine, 4-thiouridine, wybutosine, wybutoxosine, 4-acetylcytidine, 5-(carboxyhydroxymethyl)uridine, 5'-carboxymethylaminomethyl-2-thiouridine, 5-carboxymethylaminomethylurid-ine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N-6-isopentenyladenosine, beta-D-mannosylqueosine, uridine-5-oxyacetic acid, 2-thiocytidine, threonine derivatives and others (Burgin et al., 1996, Biochemistry, 35, 14090; Uhlman & Peyman, supra). By "modified bases" in this aspect is meant nucleoside bases other than adenine, guanine, cytosine and uracil at 1' position or their equivalents; such bases can be used at any position, for example, within the catalytic core of an enzymatic nucleic acid molecule and/or in the substrate-binding regions of the nucleic acid molecule.

The term nucleoside as used herein further includes "protected nucleosides". A protected nucleoside has a protecting group, such as a 5'dimethoxytrityl group. Preferably a 5'dimethoxytrityl protected nucleoside with a free (unprotected and uncapped) 3' hydroxyl group. Protecting groups are used to prevent undesirable side reactions with reactive groups present in the nucleoside thereby allowing selective reaction at the desired location of the nucleoside or nucleotide of interest.

In one preferred embodiment, the invention provides a method for rapidly attaching a chemical moiety to a matrix comprising the steps of: (a) contacting the matrix with a reagent capable of adding thiol ester, a thioamide, a sulfonamide, a sulfonate ester a phosphoramide or phosphoric ester on the matrix; (b) exposing the reaction mixture of step (a) to microwave radiation thereby resulting in a functionalized matrix with free carboxy termini; (c) contacting the functionalized matrix of step (b) with a reagent capable of forming an ester or amide bond with the matrix and having a free carboxyl termini on the matrix; (d) exposing the reaction mixture of step (c) to microwave radiation thereby forming a mono-ester or mono-amide linkage with the matrix having free carboxyl termini; and (e) coupling the carboxylated matrix of step (d) with the chemical moiety via a functionalized region of the chemical moiety capable of reacting with the carboxylated matrix, thereby resulting in a matrix functionalized with the chemical moiety.

In yet another embodiment, the invention provides rapid functionalization of solid supports by microwave-assisted processes and their subsequent utilization in the loading of nucleosides. In this embodiment (Scheme 1), controlled pore glass support (CPG) is contacted with 3-aminopropyl-triethoxysilane, either neat or in presence of dimethylformamide (DMF) as solvent under microwave conditions. The resulting amino-functionalized CPG is then reacted with succinic anhydride in DMF under microwave conditions. The succinylated CPG is then contacted with 5'-protected nucleoside derivative, preferably 5'-dimethoxytrityl-protected nucleoside with a "free" 3'-hydroxyl group, either under microwave or without microwave conditions.

Scheme 1

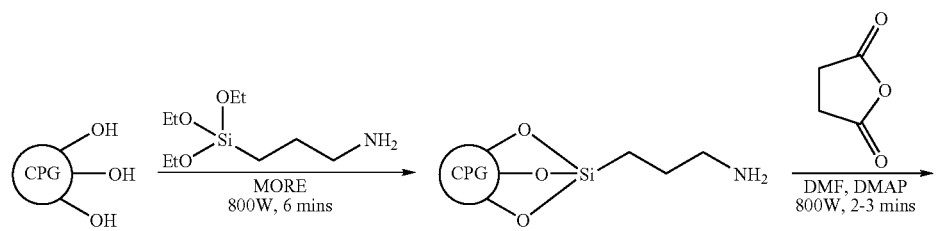

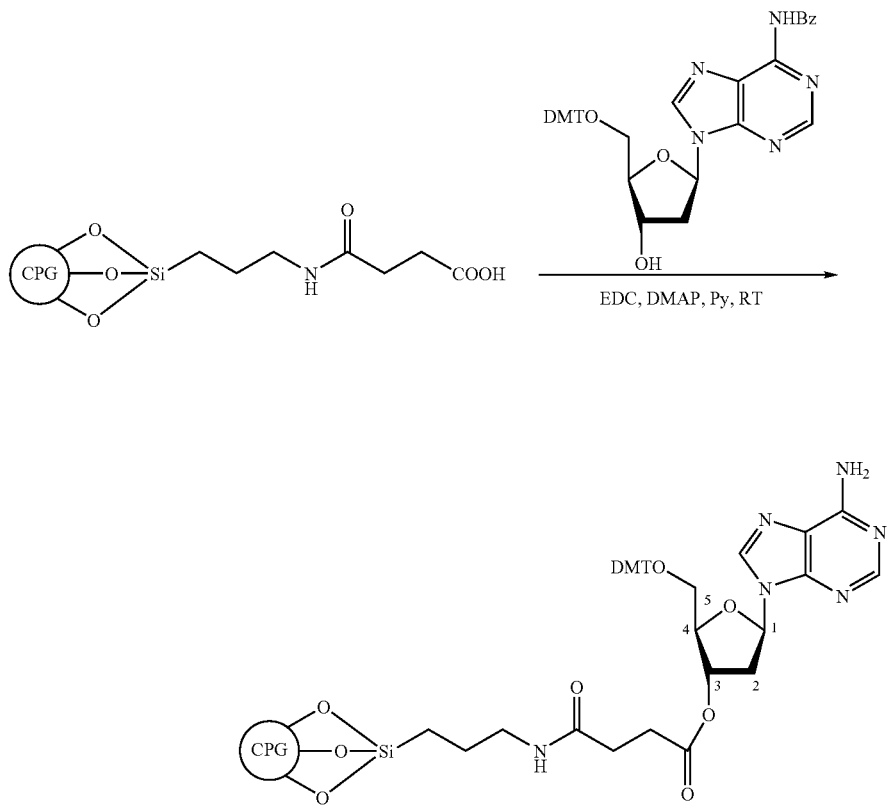

The abbreviations used in Scheme 1 are as follows: MORE, (microwave-induced organic reaction); DMAP, 4,4-dimethylaminopyridine; Py, Pyridine; DMF, Dimethylformamide; EDC, Ethyl 3-(3-dimethylaminopropyl)carbodimide.

Thus, in a preferred embodiment, the invention provides a method for preparing a functionalized matrix for oligonucleotide synthesis comprising the steps of: (a) contacting the matrix with a reagent capable of adding an amino functional group to the matrix; (b) exposing the reaction mixture of step (a) to microwave radiation thereby resulting in an amino-functionalized matrix; (c) contacting the amino-functionalized matrix of step (b) with a succinylating reagent capable of chemically succinylating the matrix; (d) exposing the reaction mixture of step (c) to microwave radiation thereby resulting in a succinylated matrix; (e) coupling the succinylated matrix with a nucleoside derivative capable of reacting with the succinylated matrix thereby forming a functionalized matrix suitable for further use in the synthesis of oligonucleotides; and (f) optionally recovering excess nucleosides used step (e).

In one preferred embodiment, step (e) above, further comprises the use of a solvent such as DMF for coupling of nucleosides to the succinylated matrix.

In another preferred embodiment, step (f) is carried out by collecting the filtrate from the reaction in step (e) and coupling excess nucleosides onto succinylated supports during aqueous work up of the filtrate.

In all relevant embodiments described herein, examples of suitable succinylating reagents include but are not limited to succinic anhydride, substituted dicarboxylic acids such as substituted succinic acid, substituted glutaric acid and their corresponding anhydrides, or a reagent capable of forming a mono-ester linkage with the matrix and having a free carboxyl termini group.

As used herein, a reagent capable of adding an amino functional group to a matrix is known as an "aminating reagent". Suitable aminating reagents useful in all relevant embodiments of the invention include but are not limited to, 3-amino-alkyl silane, 3 amino-propyl-dimethyl-ethoxy silane, or N-[3-triethoxysilyl)propyl]ethylene diamine.

In one embodiment, a matrix with a predetermined loading capacity (often low-loaded supports) may be obtained by using a mixture of two reagents, one of which will serve as the aminating reagent and the other serves as the filling agent (e.g. phenyltriethoxy silane). The reaction of the filler agent (or capping reagent) with the nucleophilic groups on the support results in a modified support that lacks a reactive functional terminus (such as an amino group). Consequently the filled or capped site on the matrix is not available for nucleoside derivatization. At the same time, the reaction of the aminating reagent with the support results in an amino-terminated support which can react with other functional groups such as a carboxyl group.

The processes of the invention can be utilized without limitation for loading of nucleosides on a variety of commercially available matrices such as controlled pore-glass (CPG), polystyrene, tentagel, polyethylene glycol based (PEGA) supports and the like. Typically the reaction is performed in industrial microwave equipment suitable for chemical reactions or even a domestic microwave with the proper equipment. In one embodiment of the invention, reactions are performed for 3 to 4 minutes in one stretch. In another embodiment of the invention, reactions are performed in pulsed intervals of up to 30 seconds each followed by wait period of 5 minute. Preferably, the total microwave exposure time is about 4 to 6 minutes.

Typical loadings of amino groups by microwave-assisted procedures in accordance with the invention have ranged from 80 to 120 micromol/g. Nucleoside loadings of up to 90 micromole/g has been achieved in accordance with the invention. These loadings are much higher than loadings obtained by prior art protocols. Using prior art protocols, the nucleoside loadings only of 30 to 50 micromol/g are usually achieved.

In another embodiment of the invention, the loading capacity of amino groups and nucleosides is enhanced by treating an amino-functionalized CPG with a bifunctional reagent such as phenyldiisothiocyanate (Scheme 2). This results in the formation of thiourea with a thioisocyanate terminus. Further reaction with polyamidoamine (PAMAM) yields CPG with multiple amino sites on the surface. The CPG can then be succinylated and loaded with nucleoside to get further ultrahigh loading.

In Scheme 2, R is a substituted or unsubstituted phenyl group or a substituted or unsubstituted alkyl group.

Thus, in one embodiment, the invention provides a method of preparing a functionalized matrix for oligonucleotide synthesis comprising the steps of: (a) contacting the matrix with an aminoalkylsilane reagent in the presence of a solvent having a dielectric constant and exposing the reaction mixture to microwave radiation thereby resulting in an amino-functionalized matrix; (b) reacting the amino-functionalized matrix of step (a) with a bifunctional reagent such as phenyldiisothiocyanate and exposing the reaction mixture to microwave radiation in the presence of solvent thereby converting the amino groups on the matrix to thiourea groups whereby the matrix is further functionalized with a thioisocyanate terminus; (c) contacting the matrix of step (b) with polyamine such as polyamidoamine and exposing the reaction mixture to microwave radiation in the presence of a solvent with a dielectric constant thereby resulting in a matrix with multiple amino sites; (d) reacting the matrix of step (c) with succinic anhydride in the presence of dimethylformamide and exposing the reaction mixture to microwave radiation thereby forming a succinylated matrix; and (e) coupling the succinylated matrix of step (d) with a 5' dimethoxytrityl-protected nucleoside derivative thereby forming a functionalized matrix suitable for further use in oligonucleotide synthesis. In another embodiment of the invention (Scheme 3), native CPG is treated with bifunctional isocyanate to generate CPG with a carbamate or thiocarbamate linkage with a terminal isocyanate or thioisocyanate moiety. Reaction with PAMAM generates CPG with multiple amino groups.

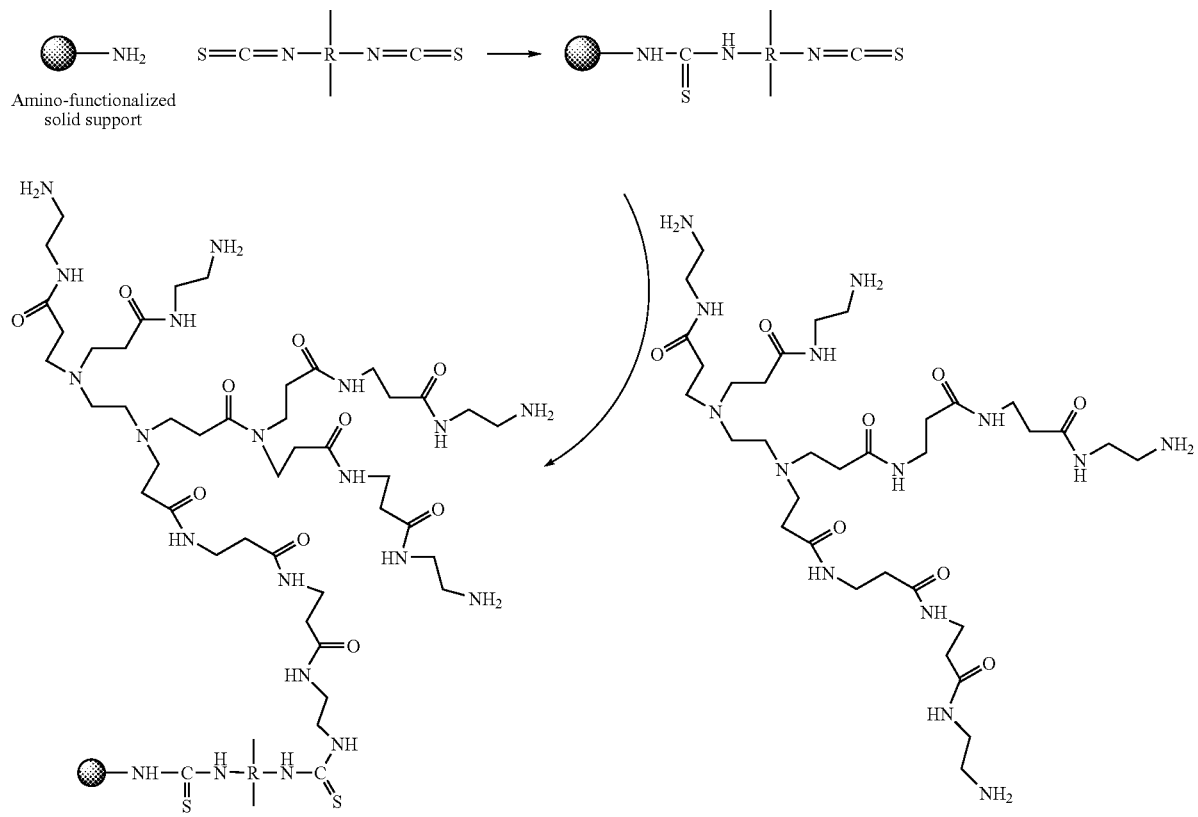

Scheme 3

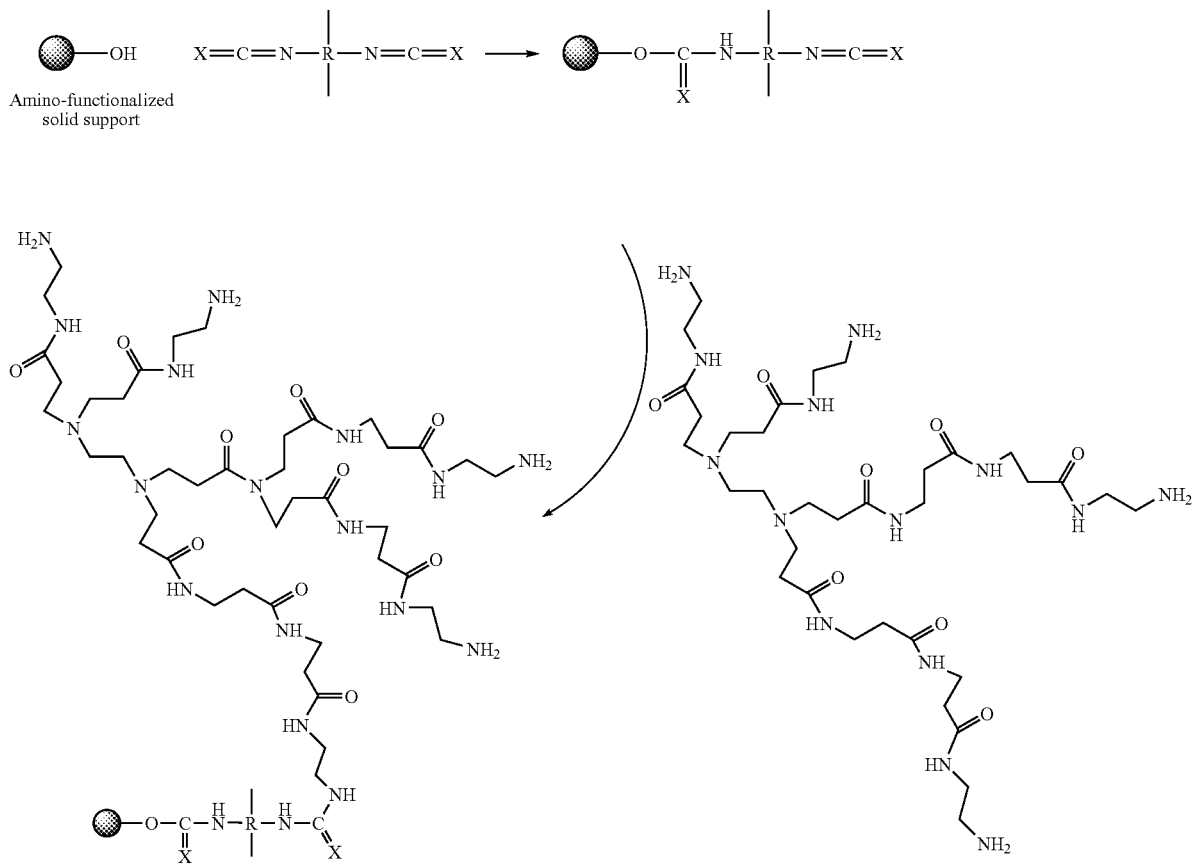

Strategy for Generation of multiple amino groups in solid supports for increased loading. CPG which contains surface hydroxyl groups is treated with bifunctional reagent directly followed by treatment with PAMAM.

In Scheme 3, X is Oxygen or Sulfur and R is as previously defined in Scheme 2.

Thus, the invention provides a method of preparing a functionalized matrix for oligonucleotide synthesis comprising the steps of: (a) contacting native CPG with bifunctional isocyanate or thioisocyanate reagent to generate CPG with a carbamate or thiocarbamate linkage with a terminal isocyanate or thioisocyanate moiety; (b) contacting the matrix from step (a) with polyamine such as polyamidoamine (PAMAM) to generates CPG with multiple amino groups; (c) reacting the matrix of step (b) with succinic anhydride in the presence of dimethylformamide and exposing the reaction mixture to microwave radiation thereby forming a succinylated matrix; and (d) coupling the succinylated matrix of step (c) with a 5' dimethoxytrityl-protected nucleoside derivative thereby forming a functionalized matrix suitablefor further use in oligonucleotide synthesis.

In another embodiment of the invention (Scheme 4), the native CPG is treated with activating groups such as p-nitrophenyl choloroformate, or carbonyldimidazole, to form the activated groups amenable to further displacement by the PAMAM.

Scheme 4

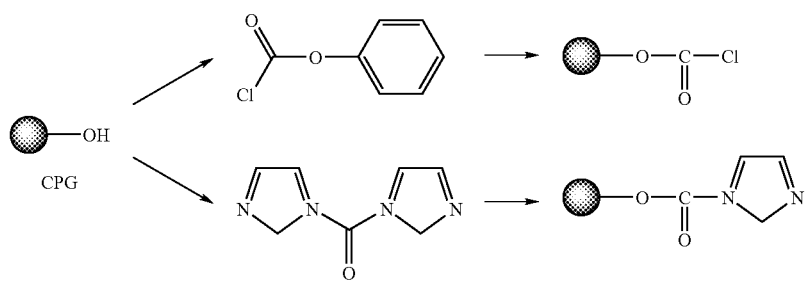

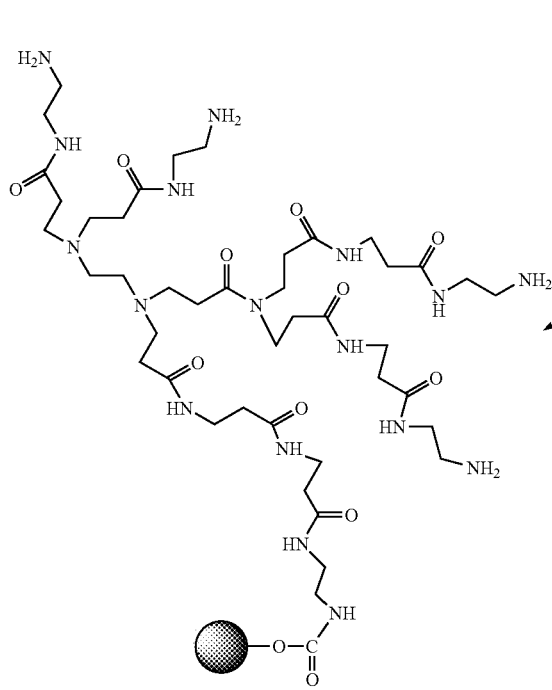 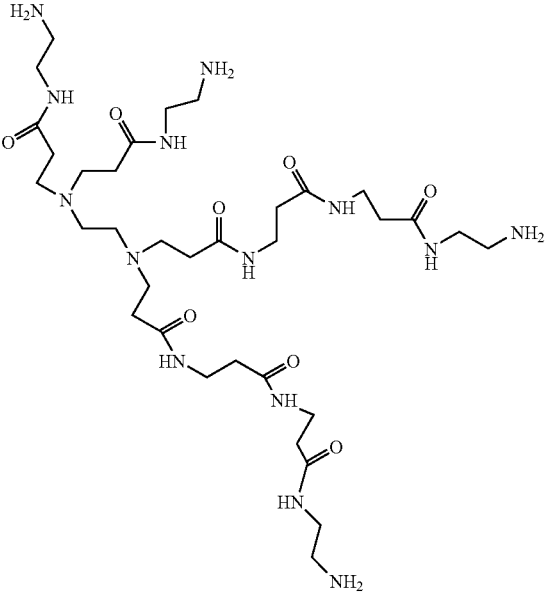

Strategy for Generation of multiple amino groups in solid supports for increased loading. CPG which contains surface hydroxyl groups is treated with activating groups followed by trestment with PAMAM.

Thus, in another embodiment, the invention provides a method of preparing a functionalized matrix for oligonucleotide synthesis comprising the steps of: (a) contacting native CPG with activating groups such as p-nitrophenyl choloroformate, carbonyldimidazole, etc to form the corresponding activated groups amenable to further displacement by amines and polyamines such as PAMAM; (b) reacting the matrix of step (a) with succinic anhydride in the presence of dimethylformamide and exposing the reaction mixture to microwave radiation thereby forming a succinylated matrix; and (c) contacting the succinylated matrix of step (b) with a 5' dimethoxytrityl-protected nucleoside derivative thereby forming a functionalized matrix suitable for further use in oligonucleotide synthesis.

In accordance with the invention, each reaction sequence is amenable to microwave conditions for rate enhancement and completion of each individual reaction sequences.

The methodologies described herein can be applied for functionalization of other solid supports[23] and loading of supports with small molecules, nucleic acids, amino acids, peptides, proteins, antibodies, carbohydrates, sugars, and other macromolecules for uses in applications selected from: peptide and carbohydrate synthesis and environmental clean up (removal of toxic materials), RIAs, FIAs, ELISA, and Affinity Chromatography. A more detailed description of the many applications for functionalized supports may be found in U.S. Pat. No. 6,486,286, incorporated herein by reference in its entirety.

The approach described here can also be employed for rapid functionalization of other solid matrices in the form of beads, slides, or pins for application in microarrays (U.S. Pat. No. 6,486,286, incorporated herein by reference in its entirety), combinatorial chemistry including medical diagnostics, environmental clean up (removal of toxic materials), radio immunoassays, fluorescent immunoassays, ELISA, and affinity chromatography.

In yet another aspect, the invention provides a functionalized matrix for oligonucleotide synthesis prepared by any one of the methods described herein. The invention further provides an oligonucleotide attached to a functionalized matrix prepared in accordance with any one of the methods of the invention described herein.

The invention further provides methods for rapid deprotection and cleavage of oligonucleotide assembled on a solid support comprising the steps of: a) taking up support-bound oligonucleotide in a heavy-walled container with a stopper; (b) adding alkali such as NaOH of strength <0.2 N, but preferably 0.1 N NaOH; c) exposing the contents to microwave radiation in 10 to 15 second cycles; d) maintaining outside temperature of the container at 90 to 95° C. while heating and 75 to 80° C. while cooling during each cycle; e) isolating the product by neutralization and filtration; and (f) separating the support for recycling. In one preferred embodiment, the separating step further comprises employing the recycled support as matrix for rapid attachment of a chemical moiety selected from nucleic acids, proteins, antibodies, carbohydrates and other macromolecules for uses in applications selected from: peptide and carbohydrate synthesis and environmental clean up (removal of toxic materials), RIAs, FIAs, ELISA, and Affinity Chromatography.

The invention is further illustrated by the following Examples.

EXAMPLES

Example 1

Rapid and efficient functionalization of solid-support by microwave-assisted procedures has been achieved. The functionalized solid-support can be readily loaded with nucleosides for use in oligonucleotide synthesis. This method can also be extended to rapid functionalization of other solid matrices for application in microarrays and combinatorial chemistry.

Over the past two decades, microwave-assisted procedures have been successfully employed in a number of synthetic transformations, resulting in rapid and efficient synthesis of different classes of organic compounds.[1] Several advantages have been claimed in the use of microwave-assisted organic synthesis[2]: (a) ultra fast reaction kinetics, (b) cleaner reactions with improved yields and reduced formation of side products, (c) ability to effect, chemo-, regio-, and stereoselective transformations, (d) flexibility to perform reactions with or without solvents, (e) economical and eco-friendly processes than the corresponding conventional reactions, and (f) successful product formations in reactions that fail under conventional conditions.

Some microwave-assisted reactions pose significant risk of explosion especially when conducted in closed vessels.[2] In such cases, reactions have been conducted following deposition of reactants on solid matrix such as alumina, silica gel, and clay. Interestingly, the supports by themselves were found to absorb very little microwave energy.[3] Examples of reactions carried out on matrix-bound reactants include trans-esterfication,[4] N-acylation,[5] Ugi four-component condensation,[6] and Suzuki coupling.[7]

However, there are only limited reports of application of microwave-assisted procedures in the solid-phase synthesis of nucleic acids.[1] As is well-known, besides the actual assembly of a polynucleotide on solid support, there are two other critical steps in nucleic acid synthesis[8] (a) preparation of solid support (usually controlled-pore-glass, [CPG]) loaded with the leader nucleoside, and (b) deprotection and cleavage of the assembled, support-bound oligonucleotide. Both steps involve prolonged, labor-intensive operations. Several improvements have been reported to facilitate rapid deprotection and cleavage of oligonucleotides[8] including a recent report of microwave-assisted procedures.[9] In contrast, there are only limited reports of improved procedures for loading of nucleosides on functionalized supports and their utility has not been fully explored.

Reported methodologies[10-12] for functionalization and loading of CPG are time-consuming, labor-intensive, and involve the use of toxic solvents. Scheme 5 shows the reaction sequences for functionalization and loading of CPG[13] and involve (Path A): (a) reaction of CPG with 3-aminopropyltriethoxysilane to give the amino-functionalized CPG; (b) reaction of aminated support 1 with succinic anhydride to give carboxy-terminated CPG 2;[14] and (c) reaction of 2 with nucleoside 3 to give the nucleoside-loaded CPG 4.

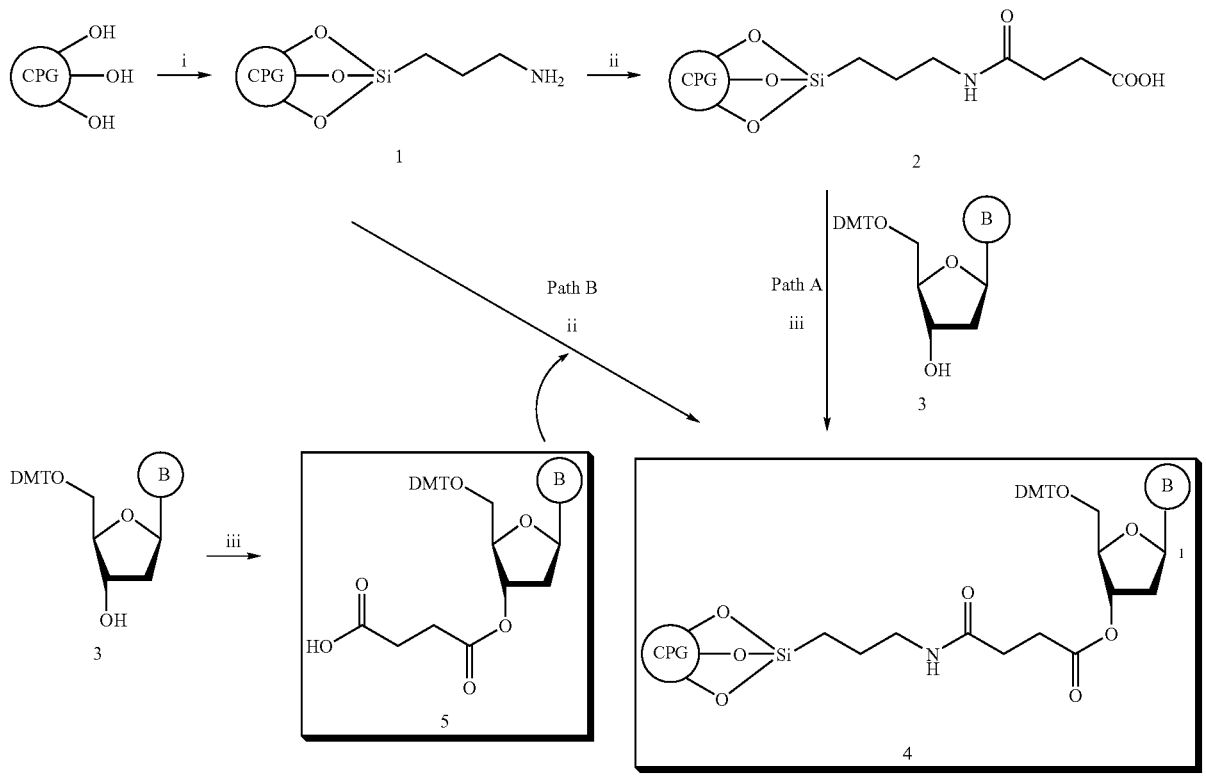

i. (3-Aminopropyl)triethoxysilane, toluene, 48 to 72 h, reflux
ii Succinic anhydride, py DMAP, 48 h, RT
iii. N-Ethyl-N'-3-(dimethylaminopropyl)carbodimide hydrochloride (EDC), DMAP, py, RT, 24 to 48 h.

Alternatively, reaction sequence in Path B has also been employed, but is less convenient especially when modified nucleosides are used because of tedious purification to obtain hemi-succinylated intermediate 5.[13] Thus, starting from native CPG, complete set of sequence of reactions require seven to 10 days to obtain nucleoside-loaded CPG 4. Consequently, availability of nucleoside-bound supports presents a significant bottleneck in the synthesis and manufacture of oligonucleotides.

We report here the use of microwave-assisted procedures for ultra fast functionalization of solid supports that enable rapid loading of nucleosides on solid supports.

I. Microwave-Assisted Amination (MAA) of CPG

Using reported procedures,[10-12] we attempted the amination of CPG (500 A, Prime Synthesis) by treatment with (3-aminopropyl)triethoxysilane (APTES) in toluene for 48 to 72 h, followed by capping of unreacted hydroxy groups with trimethylsilyl chloride. Referring to Scheme 5, although aminopropyl-CPG 1 could be isolated from the reaction, the heterogeneous amination reaction had to be performed in refluxing toluene and was unmanageable. Also, on some occasions, after capping of unreacted hydroxyl groups with trimethylsilyl chloride, the product isolated was found to be devoid of amino group. This prompted us to investigate MAA of CPG for the preparation of 1 using a domestic microwave oven (800 watts, High power setting).

For conducting MAA of CPG, (Scheme 5) a specially fabricated heavy-walled glass chamber was employed. The chamber was fitted with Teflon screw cap with a chemically resistant o-ring. These microwave reactions should not be attempted in common laboratory glassware. All microwave reactions should be carried out behind safety shields. Typically, the MAA of slurry of CPG (50 to 100 g) in APTES gave the aminated product 1 within a few minutes. Following filtration and washing, aminated-CPG 1 with amino-loadings of 90 to 113 micromol/g was obtained. Typically 3.5 mL APTES/g of CPG was employed. In all cases, the desired aminopropyl CPG was isolated after washings with toluene, methanol, dichloromethane and hexanes. Amino-loading was determined by standard protocol[13] by treating a known amount of support with DMTrCl and $Bu_4N^+ClO_4$ and "trityl assay"[13] was carried out on the resulting DMTr derivative. In order to ascertain if amino-loading of CPG could be further increased, the initially formed 1 was subjected to MAA with APTES. However, no further increase in loading resulted thereby suggesting that all available hydroxyl groups on the CPG had been functionalized during the first reaction. Thus, amination of CPG was completed within a few minutes under microwave conditions.

We also evaluated the effect of different solvents on the MAA of CPG with APTES, and the results are given in Table 1.

TABLE 1

Effect of solvents on microwave-assisted amination of CPG

| Amination Reagent | Solvent | Loading µmol/g |
|---|---|---|
| APTES | DMF | 86 |
|  | DMSO | 116 |
|  | Neat | 113 |

Although MAA could be conducted in DMF and DMSO, we found that reaction using slurry of CPG with APTES to be most convenient and also eco-friendly. Since APTES was used in excess in such a protocol, we attempted to use the recovered APTES in a subsequent MAA of CPG. However, MAA of CPG with recovered APTES was unsuccessful, probably due to the contamination of APTES with the liberated ethanol.

In attempts to further increase the amino-loading of CPG, we carried out MAA reactions (all neat) in conjunction with other amination agents such as (3-aminopropyl)trimethoxysilane (APTMS), and N-(3-trimethoxysilylpropyl)ethylenediamine (APTED) (Scheme 6).

Scheme 6

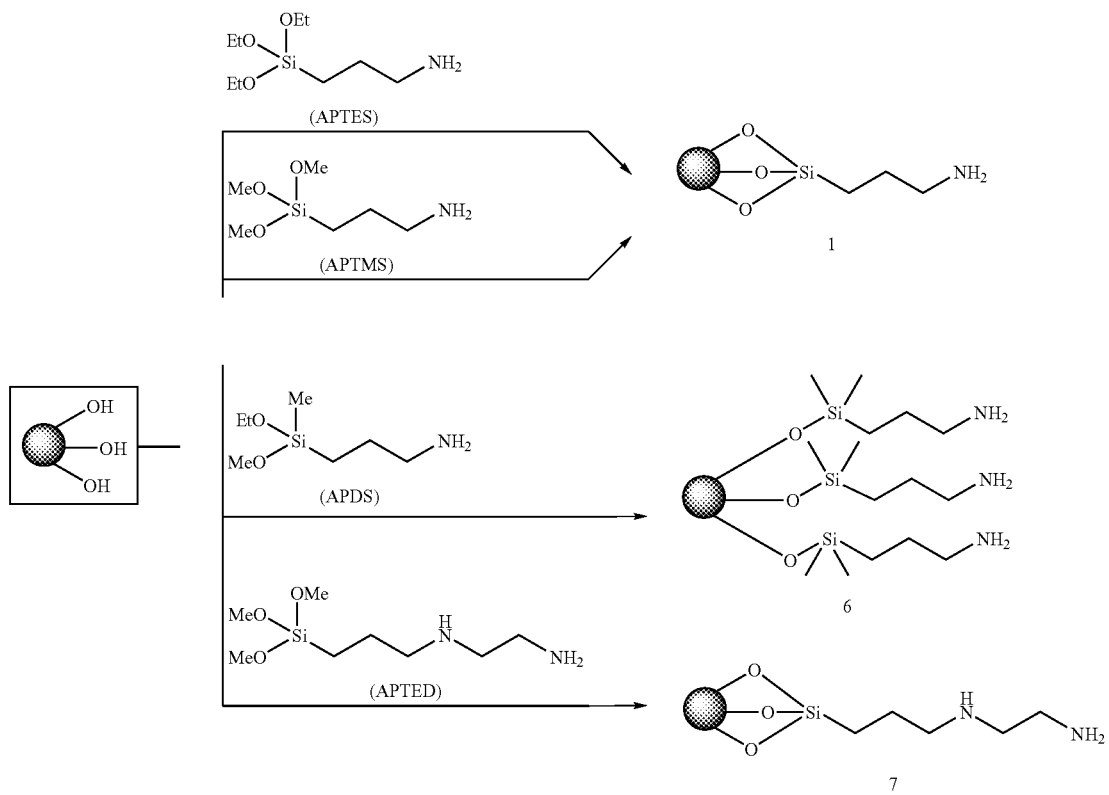

Although the corresponding aminated CPG 1 and 7 were obtained, loading was not increased beyond that obtained with APTES. Without being held to any theory, it is believed that amination involves the condensation of three hydroxyl groups on the CPG matrix, with the three ethoxy groups of APTES to form 1. We rationalized that if each of the hydroxyl groups of CPG could be engaged in reaction with a single molecule of a monoethoxysilane derivative, e.g. 3-aminopropyldimethylsilane (APDS), amino-CPG 6 with increased amino-loading could result. However, although MAA reaction of CPG with (3-aminopropyl)dimethylsilane (APDS) gave the corresponding aminated product 6, the loading was not increased beyond 96 micromol/g (Table 2).

TABLE 2

Loading of CPG obtained using microwave-assisted amination

| Amination reagent | Reaction conditions | Amino-loading micromol/g |
|---|---|---|
| 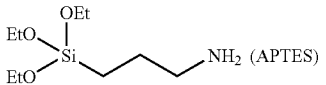 OEt, EtO, Si, NH₂ (APTES) | Condition i, from FIG. 1 | 73 |
| 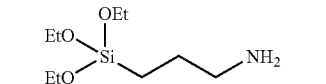 OEt, EtO, Si, NH₂ | MAA, 5 min | 98-113 |
| 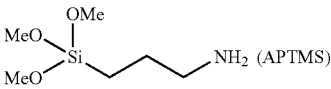 OMe, MeO, Si, NH₂ (APTMS) | MAA, 5 min | 110 |
| 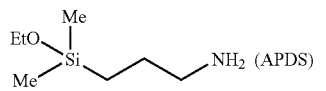 Me, EtO, Si, NH₂ (APDS) | MAA, 5 min | 96 |
| 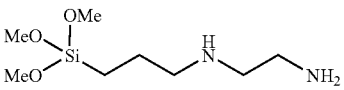 OMe, MeO, Si, H, N, NH₂ | MAA, 5 min | 79 |

In another experiment, following the first MAA with APDS, the resulting amino-CPG was further subjected to a second MAA using APTES, but there was no further improvement in loading suggesting that all available sites on the CPG had been functionalized at the first reaction itself as before.

We also evaluated the MAA of CPG with APTES using different additives (Table 3).

TABLE 3

Effect of additives on microwave-assisted amination of CPG

| Reagent | Additive | Loading (μmol/g) |
|---|---|---|
| APTES | BF₃•Et₂O | 45 |
|  | PTSA | 128 |
|  | TFA | 116 |
|  | DMAP | 110 |

Best results were obtained with p-toluene sulfonic acid and TFA giving 1 with amino loadings of 128 and 116 micromol/g respectively. With boron trifluoride etherate as a catalyst, the product 1 had considerably reduced loading (~40 μmole/g).

During the MAA of CPG with APDS, in the presence of tin (IV) chloride as a catalyst, an explosive reaction resulted. It is interesting to note that various metallic halides such as $AlCl_3$, [15] $CuBr$,[16] $FeCl_3$,[17] $BiCl_3$,[18] $ZnCl_2$,[19,20] $InCl_3$,[21] and $TaCl_3$[22] have been apparently safely employed in microwave-assisted synthetic reactions. Our results suggest that additives and solvents influence the amino loading on CPG and hence the final loading of nucleosides. Further investigation is in progress to prepare amino-CPG with a predetermined loading level.

II. Microwave-Assisted Succinylation (MAS) of Aminated CPG (1) with Succinic Anhydride Encouraged by the success in MAA of CPG, the MAS of the functionalized support 1 (Scheme 5) were attempted under microwave conditions. Microwave-assisted reaction of 1 with succinic anhydride, without the aid of any solvent, resulted in a very dark yellow colored support, probably due to the formation of imide rather than the expected acid. Nevertheless, MAS of 1 (50 to 100 g scale) was achieved successfully to give 2, in the presence of catalytic amount of DMAP in DMF as solvent, in less than 5 min. Typically 0.4 g of succinic anhydride and 50 mg of N,N-Dimethylaminopyridine each per one g of aminated CPG was employed for MAS. Since this reaction was exothermic, each microwave exposure was carried out in 30 sec cycles with intermittent cooling. After the reaction, the colored slurry was filtered, washed with dichloromethane, methanol, and hexanes, and dried. Similar results were obtained with Tentagel and PEGA resins. Completion of reaction was ascertained by testing for the absence of amino group on a sample of 1. The use of DMF in place of pyridine under microwave conditions makes MAS procedure highly attractive for the preparation of succinylated CPG 2. In addition to DMF, the succinylation can also be carried out using DMSO, dimethylacetamide, or $CH_3CN$.

III. Coupling of Nucleoside to the Succinylated CPG (2):

With the succinylated support 2 in hand, we carried out the loading of nucleosides using EDC, DMAP, and TEA (Scheme 5). When 2 was mixed with 5'-O-DMT-deoxyadenosine (3, B=dA), DMAP, TEA, and EDC (in that order) in anhydrous pyridine and shaken in an orbital shaker, CPG 4 with high nucleoside loadings of 70 to 75 micromol/g was obtained. Similar results were obtained with 5'-O-DMT-T (3, B=T).

In separate experiments, we have found that anhydrous DMF could be used instead of pyridine for the loading of nucleosides on 2. The use of DMF provides an eco-friendly alternative to pyridine. In addition, high loading of nucleoside (high-loaded CPG, 4) could be achieved when loading was carried out in a specially fabricated reactor, mounted on a rotary shaker, and with added provision for recycling of reactants (see copending U.S. Ser. No. 60/574,465, 60/583,414, 60/626,597 and 60/647,734) referred to herein as the "novel reactor." Thus, using the recycling approach, significantly less molar excess of nucleoside could be used to achieve the same loading levels as compared to the conventional protocol. This could be due to efficient mixing of the solid and liquid phases brought about by the rotary motion in the reactor in conjunction with the recycling process.

Microscopic examination revealed that microwave exposure did not affect the porosity, particle size or other physical characteristics of the CPG. To confirm this, automated synthesis of polynucleotides (using Expedite 8909 synthesizer) was carried out as below:

IV. Synthesis of Oligonucleotides:

The CPG-loaded nucleoside 4 prepared as above and the corresponding CPG prepared by conventional method[10-13] was employed in the 10 micromol synthesis of di- and 20-mer oligonucleotide (PO and PS) in an Expedite Synthesizer using phosphoramidite chemistry.[8] In both instances, the stepwise coupling yields was greater than 98% (as ascertained by trityl analysis). Following the synthesis, each of the CPG was treated with 28% NH$_4$OH at 55° C. for 12 h to isolate the fully deprotected di-, and polynucleotides. RP-HPLC analysis of crude mixture showed the profile of compounds prepared using both supports were similar.

In conclusion, a microwave assisted protocol for rapid and efficient functionalization of CPG has been achieved whereby CPG 2 carrying a carboxy-terminus could be obtained from native CPG within few hours, in contrast to the conventional procedures, which required several days. Efficient processes for loading of nucleosides on the resulting functionalized support 2 have also been achieved herein using anhydrous DMF as a solvent. Furthermore the use of a novel reactor in conjunction with recycling technology enabled efficient loading of the nucleoside on support.

References

1. For a review see: Listrom, P.; Tierney, J.; Wathey, B.; Westeman, J. *Tetrahedron*, 2001, 57, 9225-9283.
2. For a review see: Bose, A. K.; Manhas, M. S.; Ganguly, S. N.; Sharma, A. H.; Banik, B. K. *Synthesis*, 2002, No. 11, 1578-1591.
3. (a) Loupy, A.; Petit, A.; Hamelin, J.; Texier-Boullet, F.; Jacquault, P.; Mathe, D. *Synthesis*, 1998, No. 9, 1213. (b) Chatti, S.; Bortolussi, M.; Loupy, A. *Tetrahedron*, 2001, 57, 4365-70.
4. Vanden Eynde, J. J.; Rutot, D. *Tetrahedron*, 1999, 55, 2687-2694.
5. Yu, A. M.; Zhang, Z. P.; Yang, H. Z.; Zhang, C. X.; Liu, Z. *Synth. Commun.* 1999, 29, 1595-1599.
6. Hoel, A. M. L.; Nielsen, J. *Tetrahedron Lett.* 1999, 40, 3941-3944.
7. Larhed, M.; Hallberg, A. *J. Org. Chem.* 1996, 61, 9582-9584.
8. For a review see: Beaucage, S. L.; Iyer, R. P. *Tetrahedron*, 1992, 48, 2223-2311.
9. Kumar, P.; Gupta, K. C. *Nucl. Acids Res.* 1997, 25, 5127-29.
10. Majors, R.; Hopper, M. *J. Chrom. Sci.* 1974, 12, 767-778.
11. Tundo, P.; Venturello, P. *J. Am. Chem. Soc.* 1979, 101, 660-6613.
12. Matteucci, M. D. Caruthers, M. H. *Tetrahedron Lett.* 1980, 21, 719-722.
13. Pon, R. T. In *Attachments of Nucleosides to Solid-phase Supports;* Beaucage, S. L.,
Bergstrom, D. E., Glick, G. D., Jones, R. A. Current Protocols in Nucleic Acids Chemistry. John Wiley; New York, 1999; pp 287-298.
14. Damha, M. J. ; Giannaris, P. A. ; Zabarylo, S. V. *Nucl. Acids Res.* 1990, 18, 3813-21.
15. Villemin, D.; Vlieghe, X. *Sulfur Lett.* 1998, 21, 199-203.
16. Grigor'ev, A. D.; Dmitrieva, N. M.; El'tsov, A. V.; Ivanov, A. S.; Panarina, A. E.; Sokolova, N. B. *J. Gen. Chem.* 1997, 67, 981-982.
17. Vilemin, D.; Sauvaget, F. *Synlett* 1994, 435-436.
18. Baruah, M.; Prajapati, D.; Sandhu, J. S. *Synth. Commun.* 1998, 28, 4157-4163.
19. Garrigues, B.; Laurent, R.; Laporte, C.; Laporterie, A.; Dubac, *J. Liebigs Ann.* 1996, 5, 743-744.
20. Clarke, D. S.; Wood, R. *Synth. Commun.* 1996, 26, 1335-1340.
21. Ranu, B. C.; Hajra, A.; Jana, U. *Tetrahedron Lett.* 2000, 41, 531-533.
22. Chandrasekhar, S.; Padmaja, M. B.; Raza, A. *Synlett* 1999, 10, 1597-1599.
23. Other solid supports such as Tentagel™ and aminomethyl-polystyrene also could be functionalized using this protocol. Unpublished results.

Example 2

Amination of CPG:

In a pressure chamber equipped with a Teflon plug and a chemically resistant O ring (Chemraz), 3-aminopropyltriethoxysilane (APTES, 450 ml, ~3.5 ml/g) was added to Native CPG 500 CPG (135 g) and this well mixed reaction mixture was heated in a house-hold microwave (800 watt) in 1 min cycle for 8 mins. The contents of reaction mixture was mixed well by shaking between the heating cycles and allowed to cool intermittently. At the end of heating, the reaction mixture was allowed to cool to RT, filtered, washed with toluene (2×125 ml) followed by methanol (2×250 ml), dichloromethane (2×250 ml) and finally with hexanes (2×250 ml). Washed sample was treated with drops of ninhydrin and heated and the presence of amino group was indicated by strong purple color. The aminated CPG was dried in a glass tray and a small sample was dried under high vacuum overnight for amine loading by reported procedure through dimethoxytrityl content analysis as follows.

Trityl analysis: To ~100 mg of dried amino CPG, added 1 ml each of DMTrCl (0.25M in DCM) and of Bu$_4$N$^+$ClO$_4$$^-$ (0.25 M). The mixture was mixed well in an orbital shaker for 30-40 mins, filtered, washed with DCM (2×10 ml), MeOH (2×10 ml) and again with DCM (2×10 ml). Finally this tritylated aminoCPG sample was dried under high vacuum for 3 hours at r.t. Amino loading was determined following the reported protocols through trityl estimation and was found to be in the range between 100-115 micromol/g.

Succinylation of Aminopropyl CPG:

In a 500 ml pressure chamber with a Teflon screw cap stopper (with a Chemraz O ring), aminopropylCPG (150 g) was taken followed by the addition of a solution of succinic anhydride (SA, 60 g) 4-Dimethylaminopyridine (DMAP, 6 g) in N,N-Dimethylformamide (DMF, 550 ml). The reaction mixture was heated in the MW for 8-10 cycles of each 30 sec duration. Dark colored reaction mixture was mixed well by shaking at the end of each cycle and allowed to cool between the heating cycles. At the end of heating cycles, the reaction mixture was allowed to cool to RT, a small sample was filtered, washed with methanol, DCM and hexanes (10 ml each). This sample supported was tested for the completion of succinylation by adding ninhydrin solution in ethanol and heating with heatgun. Absence purple color indicated the completion of succinylation. If any trace purple color appeared, the heating cycle was continued for few more cycles and repeat the test by filtering a sample, washing and doing the ninhydrin test again.

After completion of reaction, the colored reaction mixture was filtered, washed with methanol (3×200 ml), DCM (3×200 ml), EtOAc (3×200 ml) and finally with hexanes (3×200 ml.

Loading of Nucleoside on to Succinylated CPG:

Example: Coupling of 5'-DMT-N-bzdA to Succinylated CPG

To succinylated CPG (65 g, 87 μmol/g amino loading) in a 1 lit single necked r.b. flask, was added freshly distilled anhydrous DMF (260 ml) (anhydrous DMF was prepared by distillation of dry DMF from CaH2)followed by the addition of DMT-N-bzdA (18.7 g, 5 eq), DMAP (3.5 g), TEA (4 ml) and finally EDC (5.47 g, 5 eq). The reaction flask was sealed with a rubber septa and mixed under orbital shaking (~150 rpm) overnight. If the determined loading of a representative sample from the reaction was acceptable (>65 μmol/g), the reaction mixture was filtered, washed twice with methanol, DCM and hexanes (200 ml each) and dried in air overnight. The nucleoside loaded CPG was mixed under orbital shaking with 325 ml each of CAP A and CAP B mixtures for 3 hours and the capped support was filtered, washed twice with methanol, DCM and hexanes (300 ml each). The loading of dried support was determined as 70-75 µmol/g and stored at 4° C.

Nucleoside 2: Coupling of 5'-DMT-dT to Succinylated CPG

To succinylated CPG (5 g, 110 µmol/g amino loading) in a 100 ml single necked r.b. flask, added DMF (20 ml) followed by the addition of DMTdT (1.5 g, 5 eq), DMAP (0.35 g), TEA (0.5 ml) and finally EDC (0.52 g, 5 eq). The contents of the flask were mixed under orbital shaking (~150 rpm) overnight. After the determination of initial loading (>65 µmol/g), the reaction mixture was filtered, washed twice with methanol, DCM and hexanes (20 ml each) and dried in air overnight. The nucleoside loaded CPG was mixed with 25 ml each of CAP A and CAP B mixtures for 3 hours and the capped support was filtered, washed twice with methanol, DCM and hexanes (30 ml each). The loading of dried support was determined as 68 µmol/g and stored at 4° C.

Recovery of Excess Unreacted Nucleoside: Recovery of DMT-NbzdA

The filtrate, after the isolation of nucleoside (DMT-NbzdA, example 1) loaded CPG, was slowly added to 10 volumes of ice-cold water containing 2-5 g of sodium chloride. The solid separated was allowed to settle and filtered. The solid was washed with water, extracted in chloroform and the organic layer was washed repeatedly washed with 5% citric acid to remove any trapped DMAP, sodium carbonate solution (5%) and finally brine. The chloroform layer was dried over sodium sulfate and concentration gave the excess nucleoside in acceptable purity in % yield. The 1H-NMR of recovered DMT-N-bzdA was identical with the commercial standard sample, obtained from Reliable Biopharmaceuticals (St. Louis, Mo.).

Recovery of CPG

The CPG obtained, after the isolation of SB9000, a dinucleotide analog, was heated with 0.1 N (10 ml/g) and heated at 48° C. overnight under orbital shaking Cooled to RT, filtered, washed with water. To this added HCl (1N, 10 ml/g) and mixed at RT for 4 h in an orbital shaker. The solid support was filtered, washed twice with water, MeOH, ethyl acetate and hexanes (each 5 ml/g). The obtained support was dried at room temperature and the retention of integrity of the recycled support was established through the sequence of reactions amination, succinylation and nucleoside loading. The capped support, obtained through recycling, has been effectively reused for repeated synthesis of SB 9000.

Solid Support with Predetermined Nucleoside Loading Level

Example: Amination of CPG with a Mixture of 3-(aminopropyl)triethoxysiland (APTES) and Phenyltriethoxysilane (PTES)

1 g of CPG was mixed with APTES and PTES in different proportions and heated in a 5 or 10 ml pressure reactor for 6-7 min in 1 min cycles. At the end of heating the reaction mixture was filtered, washed thrice with methanol, DCM and hexnes (10 ml each). The aminated products were subjected to amino loading determinations. There is a strong indication of a trend and the amino loading indeed affected by the ratio of aminating reagent (APTES) and the filter (PTES). Details of different experiments are given below in Table 4.

TABLE 4

| No. | APTES (ml) | PTES (ml) | % APTES (by vol) | Amino loading (micromol/g) |
|---|---|---|---|---|
| 1 | 1 | 1 | 50 | 98 |
| 2 | 1.5 | 1 | 60 | 92 |
| 3 | 2.0 | 1 | 66 | 90 |
| 4 | 2.5 | 1 | 71 | 98 |
| 5 | 3.0 | 1 | 75 | 97 |
| 6 | 1.0 | 2.0 | 33 | 59 |
| 7 | 0.5 | 2.0 | 20 | 60 |

The aminated CPGs have been subjected succinylation reactions as previously described.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for preparing a functionalized matrix for oligonucleotide synthesis comprising the steps of: (a) contacting a matrix with a reagent capable of adding an amino functional group to the matrix; (b) exposing the reaction mixture of step (a) to microwave radiation thereby resulting in an amino-functionalized matrix; (c) contacting the amino-functionalized matrix of step (b) with a succinic anhydride capable of chemically succinylating the matrix and introducing a free carboxyl termini onto the amino-functionalized matrix; (d) exposing the reaction mixture of step (c) to microwave radiation thereby resulting in a succinylated matrix comprising a free carboxyl termini; and (e) coupling the succinylated matrix with a nucleoside capable of reacting with said free carboxyl termini of the succinylated matrix thereby forming a functionalized matrix for oligonucleotide synthesis.

2. The method of claim 1 wherein the contacting of step (a) is carried out in a solvent having a dielectric constant.

3. The method of claim 1 wherein the reagent of step (a) capable of adding an amino functional group is an aminoalkylsilane.

4. The method of claim 2 wherein the solvent is selected from the group of dimethylformamide, dimethyl acetamide, N,N-dialkyl formamides and acetamides, N-methyl pyrrolidone, and DMSO.

5. The method of claim 1, wherein the nucleoside in the coupling step (e) is in excess, and said method further comprises a step of recovering the excess nucleoside by aqueous work up of a filtrate obtained from filtering a reaction mixture of step (e).

6. The method of claim 1 wherein the matrix is selected from the group consisting of: controlled pore glass; glass beads; glass powders; silica gels; alumina; polystyrene; polyethylene glycol; cellulose, ceramics, zeolite, clay, titanium (Ti), Carbon, silicon (Si), and gold.

7. The method of claim of claim 1 wherein the matrix is controlled pore glass.

8. The method of claim 5 wherein the nucleoside is a 5'-protected nucleoside derivative.

9. The method of claim 8 wherein the 5' nucleoside derivative is 5'-dimethoxytrityl-protected nucleoside with a free 3' hydroxyl group.

10. The method of claim 8 wherein the functionalized matrix comprises a loading of the nucleoside derivative in the range of about 60-100 micromoles of nucleoside derivative per gram of matrix.

11. The method of claim 1 wherein the amino-functionalized matrix of step (b) comprises a loading of amino group in the range of about 60-120 micromole of amino group per gram of matrix.

12. The method of claim 1 further comprising contacting the matrix with at least one more reagent capable of adding amino functional groups to the matrix after step (a) and prior to step (b).

13. A method of preparing a functionalized matrix for oligonucleotide synthesis comprising the steps of: (a) contacting the matrix with an aminoalkylsilane reagent in a solvent having a dielectric constant to obtain a reaction mixture, and exposing the reaction mixture to microwave radiation thereby resulting in an amino-functionalized matrix; (b) reacting the amino-functionalized matrix with succinic anhydride in dimethylformamide to obtain a reaction mixture of step (b), and exposing the reaction mixture of step (b) to microwave radiation thereby forming a succinylated matrix;

and (c) contacting the succinylated matrix with a 5' dimethoxytrityl-protected nucleoside derivative thereby forming a functionalized matrix for oligonucleotide synthesis.

* * * * *